United States Patent [19]

Wang et al.

US005582968A

[11] Patent Number: 5,582,968
[45] Date of Patent: Dec. 10, 1996

[54] BRANCHED HYBRID AND CLUSTER PEPTIDES EFFECTIVE IN DIAGNOSING AND DETECTING NON-A, NON-B HEPATITIS

[75] Inventors: Chang-Yi Wang, Great Neck; Barbara H. Hosein, New York, both of N.Y.

[73] Assignee: United Biomedical, Inc., Hauppauge, N.Y.

[21] Appl. No.: 946,054

[22] Filed: Sep. 15, 1992

Related U.S. Application Data

[63] Continuation-in-part of Ser. No. 719,819, Jun. 24, 1991, which is a continuation-in-part of Ser. No. 667,275, Mar. 11, 1991, abandoned, which is a continuation-in-part of Ser. No. 651,735, Feb. 7, 1991, and a continuation-in-part of Ser. No. 805,374, Dec. 11, 1991, Pat. No. 5,436,126, which is a division of Ser. No. 558,799, Jul. 26, 1990, Pat. No. 5,106,726, which is a continuation-in-part of Ser. No. 510,153, Apr. 16, 1990, which is a continuation-in-part of Ser. No. 481,348, Feb. 16, 1990, abandoned.

[51] Int. Cl.$^6$ .......................... C12Q 1/70; C07K 17/089; A61K 39/29
[52] U.S. Cl. .............. 435/5; 530/324; 530/325; 530/326; 530/327; 530/328; 424/189.1; 424/228.1
[58] Field of Search ................ 435/5; 530/324–328; 424/228.1, 189.1

[56] References Cited

U.S. PATENT DOCUMENTS

| | | | |
|---|---|---|---|
| 5,106,726 | 4/1992 | Wang | 435/5 |
| 5,191,064 | 3/1993 | Arima et al. | 530/324 |
| 5,229,490 | 7/1993 | Tam | 530/324 |
| 5,229,491 | 7/1993 | Habets et al. | 530/326 |

FOREIGN PATENT DOCUMENTS

| | | |
|---|---|---|
| 0318216 | 5/1989 | European Pat. Off. . |
| 0388232 | 9/1990 | European Pat. Off. . |
| 0468527 | 1/1992 | European Pat. Off. . |
| 0525910 | 2/1993 | European Pat. Off. . |
| 0529493 | 3/1993 | European Pat. Off. . |
| 0531974 | 3/1993 | European Pat. Off. . |
| 0586065 | 3/1994 | European Pat. Off. . |
| WO9115516 | 10/1991 | WIPO . |
| WO9222655 | 12/1992 | WIPO . |
| WO9300365 | 1/1993 | WIPO . |
| WO9309253 | 5/1993 | WIPO . |
| WO9325575 | 12/1993 | WIPO . |

OTHER PUBLICATIONS

Sällberg et al., "Immune Response to a Single Peptide . . . ", Immunol Lett 33:27–34 (1992).
Houghten et al., "The Use of Synthetic Peptide Combinatorial . . . ," Biotechniques 13:412–421 (1992).
Geysen et al., "Cognitive Features of Continuous Antigenic . . . ," J Molec Recognition 1:32–41 (1988).
Farci et al., "Lack of Protective Immunity Against Reinfection . . . ", Science 258:135–140 (1992).
Kuo et al, (1989) Science 244:362–364, An Assay for Circulating Antibodies to a Major Etiologic Virus of Human Non–A, Non–B Hepatitis.
Arima, et al, (1989) *Gastroenterologia Japonica* 24:540–544 Cloning of a cDNA associated with acute and chronic hepatitis C infection generated from patients serum RNA.
Arima et al, (1989) Gastroenterologica Japonica 24:545–548 A lambda gt11–cDNA clone specific for chronic hepatitis C generated from pooled serum presumably infected by hepatitis C virus.
Maeno et al, (1990) *Nucleic Acid Research* 18:2685–2689 A cDNA clone closely associated with non–A, non–B hepatitis.
Reyes et al, (1990) *Science* 247:1335–1339 Isolation of cDNA from the Virus Responsible for Enterically Transmitted Non–A, Non–B Hepatitis.
Okamoto et al, (1990) *Japan J. Exp. Med.* 60:167–177 The 5'–Terminal Sequence of the Hepatitis C Virus Genome.
Kato et al, (1990) Proc. Natl. Acad. Sci. 87:9524–9528 Molecular cloning of the human hepatitis C virus genome from Japanese patients with non–A, non–B hepatitis.
Mishiro et al, (1990) Lancet 336:1400–1403 Non–A, Non–B hepatitis specific antibodies directed at host–derived epitope: implication for an autoimmune process.
Hosein et al, (1991) Proc. Natl. Acad. Sci. 88:3647–3651 Improved serodiagnosis of hepatitis C virus infection with synthetic peptide antigen from capsid protein.
Okamoto et al, (1992) *J. Gen. Virology* 73:673–679 Typing hepatitis C virus by polymerase chain reaction with type–specific primers: application to clinical surveys and tracing infectious sources.

*Primary Examiner*—Michael P. Woodward
*Attorney, Agent, or Firm*—Morgan & Finnegan, L.L.P.

[57] ABSTRACT

The present invention relates to novel branched peptides specific for the diagnosis and prevention of non-A, non-B hepatitis (NANBH), as well as hepatitis C virus (HCV) infection. More particularly, the present invention is directed to branched synthetic substituted and hybrid peptides containing at least one epitope which is effective in detecting NANBH-associated antibodies in patients with NANBH using immunoassay techniques. In addition, this invention provides immunoassays for the detection and diagnosis of NANBH using the subject peptides, vaccine compositions for prevention and treatment of NANBH or HCV infection as well as a method of treating or preventing NANBH and HCV infection.

21 Claims, No Drawings

BRANCHED HYBRID AND CLUSTER PEPTIDES EFFECTIVE IN DIAGNOSING AND DETECTING NON-A, NON-B HEPATITIS

This application is a continuation-in-part of U.S. Ser. No. 719,819, filed Jun. 24, 1991, which is a continuation-in-part of U.S. Ser. No. 667,275, filed Mar. 11, 1991, which is a continuation-in-part of U.S. Ser. No. 651,735, filed Feb. 7, 1991, and of U.S. Ser. No. 805,374, filed Dec. 11, 1991 now U.S. Pat. No. 5,436,126, which is a divisional of U.S. Ser. No. 558,799, filed Jul. 26, 1990, now U.S. Pat. No. 5,106,726, which is a continuation-in-part of U.S. Ser. No. 510,153, filed Apr. 16, 1990, abandoned, which is a continuation-in-part of U.S. Ser. No. 481,348, filed Feb. 16, 1990, abandoned.

FIELD OF THE INVENTION

The present invention relates to novel branching peptides specific for the diagnosis and prevention of non-A, non-B hepatitis (NANBH), including hepatitis C virus (HCV) infection. More particularly, the present invention is directed to branched synthetic peptides containing at least one epitope which is effective in detecting NANBH-associated antibodies in patients with NANBH using immunoassay techniques. Further, the present invention is directed to synthetic peptides which are hybrids of the peptides described herein. In addition the subject peptides can be used as antigens to elicit monoclonal or polyclonal antibodies against HCV and as immunogens in vaccines for prevention and treatment of NANBH or HCV infection.

BACKGROUND OF THE INVENTION

Non-A, non-B hepatitis (NANBH) remains the most common form of post-transfusion hepatitis, imposing a strong need for sensitive and specific diagnostic screening methods to identify potential blood donors and other persons who may be carriers of the disease. Thus, accurate screening methods are needed to permit removal of contaminated blood and blood products from the blood supply with a high degree confidence.

The etiological agent of NANBH, HCV, has been cloned and identified by several groups [Houghton et al., EP 0318216, published 5/1989; Okamoto et al. (1990) *Jpn. J. Exp. Med.* 60:167; Houghton et al., EP 0388232, published 9/1990; and Kato et al. (1990) *Proc. Natl. Acad. Sci. USA* 87:9524; Arima et al. (1989a) *Gastroenterologia Japonica* 24:540; Reyes et al. (1990) *Science* 247:1335; Arima et al. (1989b) *Gastroenterologia Japonica* 24:545; Maeno et al. (1990) *Nucleic Acids Res.* 18:2685]. The HCV genome is about 10 kilobases (kb) in length and encodes a single polyprotein which is processed into structural and non-structural proteins. From the N terminus, the polyprotein includes the capsid and envelope proteins of the structural region and the NS-1 to NS-5 proteins of the non-structural region.

While some of the antigenic regions of HCV have been identified, peptides and recombinant proteins from these regions exhibit a variable degree of sensitivity and selectivity in detection and diagnosis of NANBH carriers. Antigenic regions have been reported in the core, or capsid, protein [Hosein et al. (1991) *Proc. Natl. Acad. Sci. USA* 88:3647; UBI HCV EIA Product Insert (1990); Okamoto et al. (1990) *Jap. J. Exp. Med.* 60:223; U.S. Pat. No. 5,106,726; Takahashi et al. (1992) *J. Gen. Virol.* 73:667; Kotwal et al. (1992) *Proc. Natl. Acad. Sci. USA* 89:4486]; in the envelope, NS-1, NS-2 and NS-3 proteins [Wang et al., EP 0468527, published Jan. 29, 1992]; NS-4 protein [Houghton (1989); Kuo et al. (1989) *Science* 244:362; U.S. Pat. No. 5,106,726] and NS-5 protein [Maeno et al. (1990) *Nucleic Acids Res.* 18:2685; Wang (1992)].

In addition to HCV-derived antigens, there exist other NANBH-associated antigens that appear to be encoded by a host cellular sequence. One such antigen, known as the GOR epitope, is reactive with sera from individuals who are PCR positive for HCV [Mishiro et al. (1990) *Lancet* 336:1400].

Serological validation has been used to map epitopes within certain HCV antigenic regions as described in Wang (1992) and U.S. Pat. No. 5,106,726, each of which is incorporated herein by reference. These mapping studies employed synthetic peptides to screen well-characterized NANBH serum panels and permitted identification of strong HCV antigens. Further refinement of the epitope analysis using serological validation techniques has led to the discovery that small clusters of amino acid residues contained within longer branched peptides or fusions of peptides containing one or more epitopes from separate regions of the HCV genome provide a superior and more sensitive assay for diagnosis and detection of NANBH carriers as well as for HCV infection. Hence, the present invention permits earlier detection of NANBH seroconversion and shows improved specificity, for example, fewer false positive serum samples are detected.

SUMMARY OF THE INVENTION

The present invention relates to branched synthetic peptides for the diagnosis and detection of NANBH and HCV infection. In particular the subject peptides are provided as a peptide composition having at least one branched peptide represented by the formula

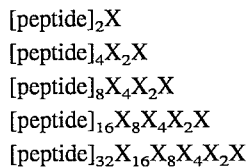

where X is an amino acid or an amino acid analog having two amino groups and one carboxyl group with each group being capable of forming a peptide bond linkage, and where the peptide moiety comprises at least one epitope which is specifically immunoreactive with antibodies against HCV. The peptide moiety further comprises at least one cluster of from about 3 to about 20 contiguous amino acids from the sequences:

Gly—Cys—Ser—Gly—Gly—Ala—Tyr—Asp—Ile—Ile—Ile—Cys—Asp—Glu—Leu—
His—Ser—Thr—Asp—Ala—Thr—Ser—Ile—Leu—Gly—Ile—Gly—Thr—Val—Leu—
Asp—Gln—Ala—Glu—Thr—Ala—Gly, (Pep3), (SEQ ID NO:1)

Phe—Thr—Phe—Ser—Pro—Arg—Arg—His—Trp—Thr—Thr—Gln—Gly—Cys—Asn—

-continued

Cys—Ser—Ile—Tyr—Pro—Gly—His—Ile—Thr—Gly—His—Arg—Met—Ala—Trp—
Asp—Met—Met—Met—Asn—Trp—Ser—Pro—Thr—Ala, (Pep8), (SEQ ID NO:2)

Glu—Ile—Leu—Arg—Lys—Ser—Arg—Arg—Phe—Ala—Gln—Ala—Leu—Pro—Val—
Trp—Ala—Arg—Pro—Asp—Tyr—Asn—Pro—Pro—Leu—Val—Glu—Thr—Trp—Lys—
Lys—Pro—Asp—Tyr—Glu—Pro—Pro—Val—Val—His—Gly—Cys—Pro—Leu—Pro—
Pro—Pro—Lys—Ser—Pro—Pro—Val—Pro—Pro—Arg—Lys—Lys—Arg—Thr,
(Pep11), (SEQ ID NO:3)

Glu—Ile—Pro—Phe—Tyr—Gly—Lys—Ala—Ile—Pro—Leu—Glu—Val—Ile—Lys—
Gly—Gly—Arg—His—Leu—Ile—Phe—Cys—His—Ser—Lys—Lys—Lys—Cys—Asp—
Glu—Leu—Ala—Ala—Lys—Leu—Val—Ala—Leu, (Pep18), (SEQ ID NO:4)

Pro—Val—Val—Pro—Gln—Ser—Phe—Gln—Val—Ala—His—Leu—His—Ala—Pro—
Thr—Gly—Ser—Gly—Lys—Ser, (Pep25), (SEQ ID NO:5)

Ser—Gly—Lys—Pro—Ala—Ile—Ile—Pro—Asp—Arg—Glu—Val—Leu—Tyr—Arg—
Glu—Phe—Asp—Glu—Met—Glu—Glu—Cys—Ser—Gln—His—Leu—Pro—Tyr—Ile—
Glu—Gln—Gly—Met—Met—Leu—Ala—Glu—Gln—Phe—Lys—Gln—Lys—Ala—Leu—
Gly—Leu, (IIH), (SEQ ID NO:6)

Ser—Gly—Lys—Pro—Ala—Ile—Ile—Pro—Asp—Arg—Glu—Val—Leu—Tyr—Arg—
Glu—Phe—Asp—Glu—Met—Glu—Glu—Cys—Ser—Gln—His—Leu—Pro—Tyr—Ile,
(IIID), (SEQ ID NO:7)

Lys—Gln—Lys—Ala—Leu—Gly—Leu—Leu—Gln—Thr—Ala—Ser—Arg—Gln—Ala—
Glu—Val—Ile—Ala—Pro—Ala—Val—Gln—Thr—Asn—Trp—Gln—Lys—Leu—Glu—
Thr—Phe—Trp—Ala—Lys—His—Met—Trp—Asn—Phe, (V), (SEQ ID NO:8)

Ser—Thr—Ile—Pro—Lys—Pro—Gln—Arg—Lys—Thr—Lys—Arg—Asn—Thr—Asn—
Arg—Arg—Pro—Gln—Asp—Val—Lys—Phe—Pro—Gly—Gly—Gly—Gln—Ile—Val—
Gly—Gly—Val—Tyr—Leu—Leu—Pro—Arg—Arg—Gly—Pro—Arg—Leu—Gly—Val—
Arg—Ala—Thr—Arg—Lys—Thr—Ser—Glu—Arg—Ser—Gln—Pro—Arg—Gly—Arg—
Arg, (VIIIE), (SEQ ID NO:9)

Asn—Asp—Arg—Val—Val—Val—Ala—Pro—Asp—Arg—Glu—Ile—Leu—Tyr—Glu—
Ala—Phe—Asp—Glu—Met—Glu—Glu—Cys—Ala—Ser—Lys—Ala—Ala—Leu—Ile—
Glu—Glu—Gly—Gln—Arg—Met—Ala—Glu—Met—Leu—Lys—Ser—Lys—Ile—Gln—
Gly—Leu, (PepA), (SEQ ID NO:10)

or a sequence corresponding to one of these sequences which is from a corresponding region in a strain or isolate of HCV. Moreover, when the peptide moiety comprises two or more clusters, the clusters are joined by a linking group or when the clusters each have a sequence from a different one of the above sequences, then the clusters can be joined directly or joined by a linking group.

When the peptide moiety contains sequences from different ones of the above sequences, such peptides are referred to as hybrid peptides. Hybrid peptides can but do not necessarily contain clusters. Clusters in hybrid peptides can be joined directly or by linking groups. In the hybrid peptides, the length of contiguous amino acids from each of the sequences can be up to about 60 residues.

Another aspect of the invention provides a method of detecting antibodies to HCV or diagnosis of HCV infection or NANBH by using an immunoeffective amount of the subject peptide composition in an immunoassay procedure, and particularly in an ELISA procedure, or a passive hemagglutination (PHA) assay. Immunoassays and kits for the detection and diagnosis of NANBH and HCV infection are also provided.

Yet another aspect of this invention provides vaccines using the subject branched hybrid and cluster peptides or peptide compositions as immunogens to prevent or therapeutically treat NANBH or HCV infection. A method of preventing or treating NANBH or HCV infection using these vaccine compositions is also provided.

DETAILED DESCRIPTION OF THE INVENTION

In accordance with the present invention, extensive epitope analysis led to the refinement and further definition of epitopes that are useful in the detection and diagnosis of NANBH and HCV infection. This analysis has established that effective diagnostic peptides for NANBH or HCV infection are branched, synthetic peptides which are hybrids of peptides containing one or more HCV epitopes from different peptides, also referred to herein as hybrid peptides. Moreover, the peptides of this invention also include branched synthetic peptides having at least one epitope which is specifically immunoreactive with antibodies against HCV and having a peptide moiety which comprises one or more clusters of about 3 to about 20 contiguous amino acids from the peptides designated as Pep3, Pep8, Pep11, Pep18, Pep25, IIH, IIID, V, VIIIE, PepA, or a homologous peptide from a corresponding region in another strain or isolate of HCV. In addition, when the peptide moiety of these peptides, also referred to herein as cluster peptides, contain two or more clusters, then the clusters are joined by a linking group. The linking group consists of, but is not limited to, one or more naturally occurring amino acids, one or more unnatural amino acids, or one or more amino acid analogues which can form peptidyl bonds (or peptidyl-like bonds) and are stable to the conditions employed during peptide synthesis. In the case of hybrid peptides that contain clusters, the clusters can be joined directly or can be joined by a linking group.

The sequences of the peptides subjected to detailed epitope analysis, and from which the peptide moieties of the subject branched peptides are derived, are set forth below:

| | |
|---|---|
| Gly—Cys—Ser—Gly—Gly—Ala—Tyr—Asp—Ile—Ile—Ile—Cys—Asp—Glu—Leu—His—Ser—Thr—Asp—Ala—Thr—Ser—Ile—Leu—Gly—Ile—Gly—Thr—Val—Leu—Asp—Gln—Ala—Glu—Thr—Ala—Gly—X, | Pep3 |
| Phe—Thr—Phe—Ser—Pro—Arg—Arg—His—Trp—Thr—Thr—Gln—Gly—Cys—Asn—Cys—Ser—Ile—Tyr—Pro—Gly—HIs—Ile—Thr—Gly—His—Arg—Met—Ala—Trp—Asp—Met—Met—Asn—Trp—Ser—Pro—Thr—Ala—X, | Pep8 |
| Glu—Ile—Leu—Arg—Lys—Ser—Arg—Arg—Phe—Ala—Gln—Ala—Leu—Pro—Val—Trp—Ala—Arg—Pro—Asp—Tyr—Asn—Pro—Pro—Leu—Val—Glu—Thr—Trp—Lys—Lys—Pro—Asp—Tyr—Glu—Pro—Pro—Val—Val—His—Gly—Cys—Pro—Leu—Pro—Pro—Pro—Lys—Ser—Pro—Pro—Val—Pro—Pro—Arg—Lys—Lys—Arg—Thr—X, | Pep11 |
| Glu—Ile—Pro—Phe—Tyr—Gly—Lys—Ala—Ile—Pro—Leu—Glu—Val—Ils—Lys—Gly—Gly—Arg—His—Leu—Ile—Phe—Cys—His—Ser—Lys—Lys—Lys—Cys—Asp—Glu—Leu—Ala—Ala—Lys—Leu—Val—Ala—Leu—X, | Pep18 |
| Pro—Val—Val—Pro—Gln—Ser—Phe—Gln—Val—Ala—His—Leu—His—Ala—Pro—Thr—Gly—Ser—Gly—Lys—Ser—X, | Pep25 |
| Ser—Gly—Lys—Pro—Ala—Ile—Ile—Pro—Asp—Arg—Glu—Val—Leu—Tyr—Arg—Glu—Phe—Asp—Glu—Met—Glu—Glu—Cys—Ser—Gln—His—Leu—Pro—Tyr—Ile—Glu—Gln—Gly—Met—Met—Leu—Ala—Glu—Gln—Phe—Lys—Gln—Lys—Ala—Leu—Gly—Leu—X, | IIH |
| Ser—Gly—Lys—Pro—Ala—Ile—Ile—Pro—Asp—Arg—Glu—Val—Leu—Tyr—Arg—Glu—Phe—Asp—Glu—Met—Glu—Glu—Cys—Ser—Gln—His—Leu—Pro—Tyr—Ile—X, | IIID |
| Lys—Gln—Lys—Ala—Leu—Gly—Leu—Leu—Gln—Thr—Ala—Ser—Arg—Gln—Ala—Glu—Val—Ile—Ala—Pro—Ala—Val—Gln—Thr—Asn—Trp—Gln—Lys—Leu—Glu—Thr—Phe—Trp—Ala—Lys—His—Met—Trp—Asn—Phe—X, | V |
| Ser—Thr—Ile—Pro—Lys—Por—Gln—Arg—Lys—Thr—Lys—Arg—Adn—Thr—Asn—Arg—Arg—Pro—Gln—Asp—Val—Lys—Phe—Pro—Gly—Gly—Gly—Gln—Ile—Val—Gly—Gly—Val—Tyr—Leu—Leu—Pro—Arg—Arg—Gly—Pro—Arg—Leu—Gly—Val—Arg—Aal—Thr—Arg—Lys—Thr—Ser—Glu—Arg—Ser—Gln—Pro—Arg—Gly—Arg—Arg—X, | VIIIE |
| Asn—Asp—Arg—Val—Val—Val—Ala—Pro—Asp—Arg—Glu—Ile—Leu—Tyr—Glu—Ala—Phe—Asp—Glu—Met—Glu—Glu—Cys—Ala—Ser—Lys—Ala—Ala—Leu—Ile—Glu—Glu—Gly—Gln—Arg—Met—Ala—Glu—Met—Leu—Lys—Ser—Lys—Ile—Gln—Gly—Leu—X | PepA | or a homologous peptide from the corresponding region in another strain or isolate of HCV, wherein X is —OH or —NH$_2$, and analogues and segments thereof.

As used herein a "cluster" is a sequence from 3 to about 20 contiguous amino acids from one of the peptide sequences described herein or an analog or segment thereof. In a preferred embodiment, a cluster has a sequence of 3 to 9 contiguous amino acids.

The branched hybrid and cluster peptides of the present invention including their analogues and segments are useful for the detection of antibodies to HCV in body fluids, the diagnosis of NANBH, and for the vaccination of healthy mammals, particularly humans, to stimulate the production of antibodies to HCV, including neutralizing or protective antibodies.

The subject branched peptides can comprise combinations or segments, i.e., longer or shorter peptide chains by having more amino acids, including unnatural amino acids, added to the terminal amino acids, or by having amino acids removed from either terminal end. For example, the sequence KKK (Lys-Lys-Lys) can be added to the amino terminus of peptides. Similarly, an M (methionine) residue can be placed at the carboxy terminus of the peptide moiety, i.e. between the peptide moiety and the branch structure.

As used herein "segments" means a shorter region of a parent peptide which retains an epitope effective in detecting NANBH-associated antibodies. For example, C10A is a segment of VIIIE, its parent peptide. A segment can be derived from either end of its parent peptide or from an internal sequence of its parent peptide.

The subject branched peptides can also comprise analogues thereof to accommodate strain-to-strain variation among different isolates of HCV or other substitutions in the prescribed sequences which do not effect immunogenicity of the epitope. HCV is indicated to have frequent mutations. Several variant strains/isolates are known to exist, such as PT, J, J1 and J4 [Houghton, 1989; Okamoto, 1990; Houghton, 1990; and Kato, 1990] and it is expected that other variant strains also exist. Adjustments for conservative substitutions and selection among the alternatives where non-conservative substitutions are involved, can be made in the prescribed sequences. The analogues of the branched synthetic peptides, especially the hybrid peptides, can therefore comprise substitutions, insertions and/or deletions of the recited amino acids of the above sequence to accommodate the various strains, as long as the immunoreactivity recognizable by the antibodies to HCV is preserved. The substitutions and insertions can be accomplished with naturally-occurring amino acids, unnatural amino acids or amino acid analogues capable of forming peptidyl bonds or peptide-like bonds (e.g., peptide thiol analogues). Analog peptides in accordance with this invention are synthesized and tested against an HCV serum panel to determine the immunoreactivity of the peptide as described hereinbelow.

Further, with appropriate amino acid modification or substitutions, it is expected that various peptide analogues based on the prescribed amino acid sequences can be synthesized with properties giving rise to lower background readings or better binding capacity to solid phases useful for HCV antibody screening assays. In particular, peptides containing unnatural amino acids can significantly reduce background readings.

The subject branched peptides can also be used to form conjugates, i.e., the peptides can be coupled directly or indirectly, by methods known in the art, to carrier proteins such as bovine serum albumin (BSA), human serum albumin (HSA), or to red blood cells or latex particles.

As used herein, natural amino acids are the 20 amino acids commonly found in proteins (i.e. alanine, aspartic acid, asparagine, arginine, cysteine, glycine, glutamine, glutamic acid, histidine, isoleucine, leucine, lysine, methionine, phenylalanine, proline, serine, threonine, tyrosine, tryptophan and valine). As used herein the natural amino acids also include the D- and L- forms of such amino acids.

As used herein "unnatural amino acids" include both D- and L- forms of any other amino acids whether found in a protein, whether found in nature or whether synthetically produced. Unnatural amino acids can include, but are not limited to, β-alanine, ornithine, norleucine, norvaline, hydroxyproline, thyroxine, gamma-amino butyric acid, homoserine, citrulline and the like.

The branched peptides of the present invention are represented by one of the formulae:

[peptide]$_2$X
[peptide]$_4$X$_2$X
[peptide]$_8$X$_4$X$_2$X
[peptide]$_{16}$X$_8$X$_4$X$_2$X
[peptide]$_{32}$X$_{16}$X$_8$X$_4$X$_2$X wherein X is an amino acid or an amino acid analog having two amino groups and one carboxyl group, each group capable of forming a peptide bond linkage. Preferably X is lysine or a lysine analog such as ornithine. The amino acid analog can be an α-amino acid, a β-amino acid, or any other either natural or non-natural amino acid with two amino groups and one carboxyl group available for forming peptide bonds. Preferred branched peptides of the invention are dimers, tetramers and octamers, especially those having a branching core structure composed of lysine, i.e. where X is lysine. Branched dimer are especially preferred.

The peptide moiety of the branched peptides can vary in length from about 10 to about 100 amino acids residues. Preferably the peptide moieties contain about 17 to about 60 amino acid residues. Moreover, the hybrid and cluster peptide moieties can be optimized to the minimal overall length necessary to contain an epitope effective in detecting NANBH-associated antibodies yet still retain the superior sensitivity and selectivity of the present invention.

The preferred branched peptides of the present invention are provided in Table 1. The source of each peptide is provided in Table 2.

TABLE 1

BRANCHED PEPTIDES[a,b]

| HYBRID PEPTIDES WITH OR WITHOUT CLUSTERS | |
|---|---|
| H1 | YEPPVVHGCPLPPPKSPPVPPPRKKRTIIPDREVLYREFDEMEECSQHLPYIPKPQRKTKRNTNRRPQDVKFPGG-GQIVG-DIM |
| H2A | LYREFDEMEDCSQHLPYIPKPNRKTKRNTQRRPNDVKFPGGGNIVGM-OCT |
| H2B | PDREILYREFDEMEDCSQHLPYIPKPNRKTKRNTQRRPNDVKFPGGGNIVGM-OCT |
| H2C | IIPDREILYREFDEMEDCSQHLPYIPKPNRKTKRNTQRRPNDVKFPGGGNIVGM-OCT |
| H2CK | IIPDREILYREFDEMEDCSQHLPYIPKPNRKTKRNTQRRPNDVKFPGGGNIVGK-OCT |
| H2D | SGKPAIIPDREILYREFDEMEDCSQHLPYTPKPNRKTKRNTQRRPNDVKFPGGGNIVGM-OCT |
| H2DK | SSKPAIIPDREILYREFDEMEDCSQHLPYIPKPNRKTKRNTQRRPNDVKFPGGGNIVGK-OCT |
| H3 | GCSGGTYDIIICDELHSTDATSIVGIGTILDQAETAGRHLIFCHTKKKCDELASKLVALGM-OCT |
| H4A | YEPPVVHGRHLIFCHTKKKCDELASKLVALGM-OCT |
| H4B | PLVETWKKPDYEPPVVHGRHLIFCHTKKKCDELASKLVALGM-OCT |
| H6A | IEQGMMLAENFKQKALGLPRRGPRLGLRATRKTTERSQPRGRM-OCT |
| H6B | SGKPAIIPEREVIEQGMMLAENFKQKALGLPRRGPRLGLRATRKTTERSQPRGRM-OCT |
| H7 | SGKPTIIPDREILYREFDEMEDCSQHLPYIDQGMMLAENFKQKALGLVKFPGGGQI-DIM |
| 3KH7 | KKKSGKPTIIPDREILYREFDEMEDCSQHLPYIDQGMMLAENFKQKALGLVKFPGGGQI-DIM |
| CLUSTER PEPTIDES | |
| C1A | IIPDREILYREFDEMEDCSQHLPYI-DIM |
| C1B | SSKPAIIPDREILYREFDEMEDCSQHLPYI-DIM |
| C2A | PLVETWKRPDYEPPVVH-OCT |
| C2B | PLVETWKKPDYEPPVVH-OCT |
| C3 | KKKSGKPTIIPDREILYREFDEMEDCSQHLPYIDQGMMLAENFKQKALGL-DIM |
| C4 | KKKIPKPNRKTKRNTQRRPNDVKFPGGGNIVGGVYLVPRRGPRLGLRATRKTTERSQPRGRR-DIM |
| C5A | DCSQHLPYIDQGMMLA-DIM |
| C5B | ILYREFDEMEDCSQHLPYIDQGMMLA-DIM |
| C5C | SGKPTIIPDREILYREFDEMEDCSQHLPYIDQGMMLA-DIM |
| 3KC5C | KKKSGKPTIIPDREILYREFDEMEDCSQHLPYIDQGMMLA-DIM |
| C6A | PLVETWKKPEYEPPVVH-DIM |
| C6B | PLVETWKKPEYEPPVVH-OCT |
| C7A | CSQHvPYIEQGMILAEQFKQKAvGL-DIM |
| C7B | LYREFDEIEECSQHvPYIEQGMILAEQFKQKAvGL-DIM |
| C7C | SGKPAvIPDREvLYREFDEIEECSQHvPYIEQGMILAEQFKQKAvGL-DIM |
| 3KC7C | KKKSGKPAvIPDREvLYREFDEIEECSQHvPYIEQGMILAEQFKQKAvGL-DIM |
| C8A | DYEPPVVH-DIM |
| C8B | PLVETWKKpDYEPPVVH-DIM |
| C8C | PLVETWKoPDYEPPVVH-DIM |
| C9A | GRHLIvCHSKKKCDEIAAKLVALG-DIM |
| C9B | EIPFYGKAvPLEvIKGGRHLIvCHSKKKCDElAAKLVALG-DIM |
| C10A | RPNDvKFPGGGNIvGGVYLVPRRGPRIGLRATRKTTERSQpRGRR-DIM |
| C10B | IPKPNRKTKRNTQRRPNDvKFPGGGNIvGGVYLVPRRGPRIGLRATRKTTERSQpRGRR-DIM |
| 3KC10B | KKKIPKPNRKTKRNTQRRPNDvKFPGGGNIvGGVYLVPRRGPRIGLRATRKTTERSQpRGRR-DIM |

[a]Abbreviations: The amino acid sequences are provided in one letter code except that unnatural amin acids are indicated by: v, norvaline; l, norleucine; p, hydroxyproline; o, ornithine. Other abbreviations are DIM, lysine dimer; OCT, lysine octamer.
[b]The branches core for these peptides is composed of lysine residues, e.g., 1 lysine for dimer peptides are 7 lysines for octamer peptides.

TABLE 2

SOURCE OF HYBRID AND CLUSTER BRANCHED PEPTIDES

| Source Peptide | Branched Peptides from Table 1 |
|---|---|
| Pep11 | C2A, C2B, C6A, C6B, C8A, C8B, C8C |
| Pep18 | C9A, C9B |
| IIH | C3, C5A, C5B, C5C, 3KC5C, C7A, C7B, C7C, 3KC7C |
| IIID | C1A, C1B |
| VIIIE | C4, C10A, C10B, 3KC10B |
| Pep3 + Pep18 | H3 |
| Pep11 + Pep18 | H4A, H4B |
| Pep11 + IIID + VIIIE | H1 |
| IIH + VIIIE | H6A, H6B, H7, 3KH7 |
| IIID + VIIIE | H2A, H2B, H2C, H2CK, H2D, H2DK |

The peptide compositions of the present invention can be composed of one or more of the branched hybrid peptides, branched cluster peptides or any combination of such peptides. Preferably such compositions contain from one to 10 branched peptides, and even more preferably from one to four branched peptides.

In a preferred embodiment, the peptide compositions of the present invention can be a mixture of branched peptides (1) C3 dimer, C9B dimer, C6A dimer and 3KH7 dimer; (2) 3K204h dimer, C4 dimer, C2B octamer; (3) C4 dimer, C9B dimer, C6A dimer and H7 dimer; or (4) 3KH7 dimer, C6A dimer and C4 dimer. The effective ratio of peptides for diagnosing or detecting NANBH or HCV present in peptide compositions containing mixtures of the subject peptides can be readily determined by one of ordinary skill in the art. Typically, these ratios range from about 1 to about 50 on a per weight basis of peptide.

An especially preferred peptide composition for diagnosis and detection of NANBH or HCV infection is mixture (1), branched peptides 3KC10B dimer, C9B dimer, C6A dimer and 3KH7 dimer in a weight ratio of 5:15:1:25.

To determine the efficacy of the subject peptides in detecting and diagnosing NANBH and HCV infection, the peptides are tested for their immunoreactivity with special specimens previously selected through the screening of thousands of patient and normal sera for immunoreactivity with HCV. Such serum panels are commercially available and examples thereof are provided in the Examples.

The strategy for serological validation depends on the expected characteristics of the target epitopes. For example, universal immunodominant epitopes, such as the gp41 transmembrane peptide of HIV-1, can be screened by a single representative serum sample from a patient known to be infected with the virus. Epitopes that are not recognized by all infected individuals, or those for which antibody is produced late or only transiently, and especially epitopes which give rise to neutralizing antibodies, must be screened by large panels of sera. While both methods of screening can be employed in the present invention to refine the epitope analysis of HCV using the subject peptides, the latter method is particularly useful in assessing the subject peptides for superior selectivity and sensitivity.

The identification of the immunoreactive epitopes is also dependent on the panel of sera used. The more closely the panel represents the population most likely to be seropositive for an epitope, the greater the chance that the epitope will be identified and thoroughly mapped. Hence, to extend the range of reactivity of an assay comprised of previously identified epitopes, a large number of samples from individuals at risk of infection but seronegative against known epitopes should be employed for screening.

The process of "serological validation" is particularly difficult when the epitopes to be identified elicit antibodies only in a subpopulation of an infected patient group. When such epitopes become targets for identification, special attention must be paid to synthetic peptides which show very weak reactivity when tested by an enzyme immunoassay or any other immunological testing method.

In this regard, the low background absorbance of synthetic peptides, especially peptides with unnatural amino acids, allows for the precise detection of weak reactivities. In some cases, absorbances of 50 mA versus background reading are of sufficient significance and can lead to the identification of important epitopes through successive refinement of the amino acid sequence of a peptide. With good laboratory practices, consistent and reliable results can be obtained when working in the range of absorbances below 200–300 mA.

Based on the immunoreactivities of the peptides of the present invention, the subject peptides are also useful in a vaccine composition to treat or prevent NANBH or HCV infection. The branched peptides, alone or when coupled to a carrier or polymerized to homo or hetero dimers or higher oligomers by cysteine oxidation, by induced disulfide cross-linking, or by use of homo or hetero functional multivalent cross-linking reagents, can be introduced into normal subjects to stimulate production of antibodies to HCV in healthy mammals. Similarly the subject branched peptides can be formulated in a vaccine composition using adjuvants, pharmaceutically-acceptable carriers or other ingredients routinely provided in vaccine compositions. Such formulations are readily determined by one of ordinary skill in the art and include formulations for immediate release and for sustained release, e.g., microencapsulation. The present vaccines can be administered by any convenient route including subcutaneous, oral, intramuscular, intravenous, or other parenteral or enteral route. Similarly the vaccines can be administered as a single dose or divided into multiple doses for administration.

The vaccine compositions of the instant invention contain an immunoeffective amount of the subject branched peptides to treat or prevent NANBH or HCV infection. Such compositions in dosage unit form can contain about 0.1 µg to about 1 mg of the peptide (or mixture of peptides) per kg body weight. When delivered in multiple doses, the dosage unit form is conveniently divided into the appropriate amounts per dosage.

The advantages of using synthetic peptides are known. Since the peptides not derived biologically from the virus, there is no danger of exposing the normal subjects who are to be vaccinated to the disease causing pathogen. The peptides can be readily synthesized using standard techniques, such as the Merrifield method of synthesis [Merrifield (1963) *J. Am. Chem. Soc.* 85:2149–2154]. Hence, there is no involvement with HCV at any time during the process of making the test reagent or the vaccine. Another problem which can be minimized by using peptides rather than recombinantly expressed proteins (or peptides) is the rate of false positive results caused by the presence of antigenic material co-purified with the HCV fusion protein. For example, certain normal individuals have antibodies to *Escherichia coli* or yeast proteins which are cross reactive with the antigenic materials from the expression system used in recombinant-based diagnostic tests. Sera from such normal individuals show a false positive reaction in such immunoassays which is eliminated in immunoassays of the present invention.

Moreover, because the peptide compositions of the present invention are synthetically prepared, the quality can be controlled and as a result, reproducibility of the test results can be assured. Also, since very small amounts of a peptide are required for each test procedure, and because the expense of preparing a peptide is relatively low, the cost of screening body fluids for antibodies to HCV, diagnosis of NANBH infection, and the preparation of a vaccine is relatively low.

The peptides and peptide compositions prepared in accordance with the present invention can be used to detect HCV infection and diagnose NANBH by using them as the test reagent in an enzyme-linked immunoadsorbent assay (ELISA), an enzyme immunodot assay, a passive hemagglutination assay (e.g., PHA test) or other well-known immunoassays. In accordance with the present invention, any suitable immunoassay can be used with the subject peptides. Such techniques are well known to the ordinarily skilled artisan and have been described in many standard immunology manuals and texts, see for example, by Harlow et al. (1988) *Antibodies: A Laboratory Manual*, Cold Spring Harbor Laboratory Press, Cold Spring Harbor, N.Y., 726 pp. In a preferred embodiment, the immunoassay is an ELISA using a solid phase coated with the peptide compositions of the present invention. ELISA techniques are well known in the art. In another preferred embodiment the immunoassay is a PHA assay.

The immunoassays of the present invention are used to screen body fluids and tissues for the presence of NANBH or HCV and thereby to detect such agents and aid the practitioner in diagnosis of NANBH or HCV infection. The body fluids which can be subjected to such screening include blood and blood fractions (e.g. serum), saliva, or any other fluid which contains antibodies against HCV.

Another aspect of the present invention is directed to a kit for the detection and diagnosis of NANBH or HCV infection in mammalian body fluids (e.g. serum, tissue extracts, tissue fluids), in vitro cell culture supernatants, and cell lysates. The kit can be compartmentalized to receive a first container adapted to contain one or more of the peptides (i.e. a peptide composition) of this invention.

Preferably the kit of this invention is an ELISA or a PHA test kit for detection or diagnosis of NANBH or HCV infection. For an ELISA test kit, the kit contains (a) a container (e.g., a 96-well plate) having a solid phase coated with one of the subject peptide compositions; (b) a negative control sample; (c) a positive control sample; (d) specimen diluent and (e) antibodies to human IgG, which antibodies are labelled with a reporter molecule. If the reporter molecule is an enzyme, then the kit also contains a substrate for said enzyme.

In an exemplified use of the subject kit, a sample to be tested is contacted with a mammalian body fluid, diluted in sample diluent if necessary, for a time and under conditions for any antibodies, if present, to bind to the peptide contained in the container. After removal of unbound material (e.g. by washing with sterile phosphate buffered saline), the secondary complex is contacted with labelled antibodies to human IgG. These antibodies bind to the secondary complex to form a tertiary complex and, since the second antibodies are labeled with a reporter molecule, when subjected to a detecting means, the tertiary complex is detected. The reporter molecule can be an enzyme, radioisotope, fluorophore, bioluminescent molecule, chemiluminescent molecule, biotin, avidin, streptavidin or the like. For ELISA the reporter is preferably an enzyme.

The examples serve to illustrate the present invention and are not to be used to limit the scope of the invention.

EXAMPLE 1

Detection of antibodies to the core region of HCV in early seroconversion sample using branched cluster peptides The wells of 96-well plates were coated separately for 1 hour at 37° with 1 µg/ml of peptide using 100 µL per well in 10 mM NaHCO$_3$ buffer, pH 9.5, for each of two branched peptides from the core region of HCV (peptide C4, Table 1; and test peptide T1 related to VIIIE and having the sequence KKKIPKPQRKTKRNTNRRPQDVKFPGGG-QIVGGVYLLPRRGPRLGVRATRKTSERSQPRGRR —DIM.

The peptide-coated wells were then incubated with 250 µL of 3% by weight of gelatin in PBS in 37° C. for 1 hour to block non-specific protein binding sites, followed by three washes with PBS containing 0.05% by volume of TWEEN 20 and then dried. The test specimens containing HCV antibody positive patient sera were diluted with PBS containing 20% by volume normal goat serum, 1% by weight gelatin and 0.05% by volume TWEEN 20 at dilutions of 1:20 volume to volume, respectively. 200 µL of the diluted specimens were added to each of the wells and allowed to react for 15 minutes at 37° C.

The wells were then washed six times with 0.05% by volume TWEEN 20 in PBS in order to remove unbound antibodies. Horseradish peroxidase conjugated goat anti-human IgG was used as a second antibody tracer to bind with the HCV antibody-peptide antigen complex formed in positive wells. 100 µL of peroxidase labeled goat anti-human IgG at a dilution of 1:1800 in 1% by volume normal goat serum, 0.05% by volume TWEEN 20 in PBS was added to each well and incubated at 37° C. for another 15 minutes.

The wells were washed six times with 0.05% by volume TWEEN 20 PBS to remove unbound antibody and reacted with 100 µL of the substrate mixture containing 0.04% by weight orthophenylenediamine (OPD) and 0.12% by volume hydrogen peroxide in sodium citrate buffer, pH 5.0. This substrate mixture was used to detect the peroxidase label by forming a colored product. Reactions were stopped by the addition of 100 µL of 1.0M H$_2$SO$_4$ and the A$_{492}$nm measured.

The sensitivity of these two peptides in detecting antibody to the core region was tested with a seroconversion panel in which the earliest antibody response is known to be against core (Serologicals Panel 4813, Donor 02190D as referenced in U.S. Pat. No. 5,106,726; early core response as referenced in Hosein, 1991). The bleed date chosen for comparison was Aug. 30, 1988. The optical density obtained with peptide C4 was 0.320 and with T1, 0.512. Both peptides were more sensitive than the linear peptide VIIIE with three lysine residues at its N terminus when coated at the same concentration, in which case the absorbance on the same sample was 0.075.

EXAMPLE 2

Branched hybrid peptides confer improved sensitivity and specificity relative to the individual peptides The immunoreactivity of branched hybrid peptide 3KH7 (Table 1) containing an epitope from the NS-4 and core regions of HCV was tested on panel 3 containing 41 known NANBH samples using the ELISA assay format as described in Example 1. Table 3 shows that this hybrid peptide retained the reactivity of both the NS-4 and the core regions as compared to octamer T2 (related to VIIIE) from the core region only and peptide T3 (related to IIH) from the NS-4 region only. Furthermore, sample 3–35 showed improved reactivity with the hybrid peptide relative to either single region peptide.

The specificity of the hybrid peptide 3KH7 was tested on a panel of 48 random blood donor samples screened negative for antibodies to HCV. Only one of the negative samples had an absorbance greater than 0.200 A with the hybrid peptide, whereas twenty percent of these samples had absorbance values greater than 0.200 A with the octamer T2. Branched cluster peptide C3, containing an epitope from the NS-4 region but lacking the core epitopes, gave absorbance values greater than 0.200 A on 5/48 negative samples. Therefore the combination of epitopes from the two regions as presented in the hybrid peptide resulted in improved specificity for detection of NANBH.

TABLE 3

| HCV Positive Sample[a] | $A_{492nm}$ (pos/neg) | | |
|---|---|---|---|
| | 3KH7 | T2[b] | T3[b] |
| 3-2 | 0.491(+) | 0.068(−) | 0.756(+) |
| 3-10 | 1.164(+) | 0.027(−) | 1.857(+) |
| 3-21 | 2.576(+) | 0.095(−) | 2.226(+) |
| 3-32 | 1.653(+) | 1.188(+) | 2.236(+) |
| 3-35 | 2.303(+) | 0.800(+) | 0.324(+) |
| 3-39 | 1.441(+) | 0.486(+) | 1.676(+) |
| 3-7 | 1.118(+) | 3.229(+) | 0.582(+) |
| 3-8 | 0.696(+) | 1.860(+) | 0.003(−) |
| 3-9 | 1.408(+) | 2.797(+) | 0.163(−) |
| 3-12 | 1.870(+) | 0.328(+) | 0.037(−) |
| 3-26 | 1.607(+) | 3.233(+) | 0.355(+) |

[a]The remaining samples in panel 3 were negative on all peptides or showed no improvement in using the branched hybrid peptide compared with the test peptides.
[b]The sequences of control peptides T2 and T3 (SEQ ID NO: 11) are, respectively, VKFPGGGQIM-octamer and KKKSGKPAIIPDREVLYREF-DEMEECSQHLPYIEQGMMLAEQFKQKALGL

EXAMPLE 3

Comparison of sensitivity and specificity in detection of NANBH-associated antibodies in branched cluster peptides with unnatural amino acids linking groups The immunoreactivity of branched cluster peptide C10B (Table 1) from the core region with clusters separated by unnatural amino acids was compared with a similar peptide T1 (Example 1) lacking such unnatural amino acids, using panel 3 samples in an ELISA assay format as described in Example 1. Table 4 illustrates seven samples in which the absorbance for the peptide containing unnatural amino acids was higher than for the corresponding peptide lacking unnatural amino acids, i.e., branched peptide C10B was more sensitive than T1. The specificity of these two peptides was equivalent with 0/48 negative samples having absorbance readings greater than 0.200 A.

The immunoreactivity of branched cluster peptide C8C (Table 1) from the NS-5 region of HCV having clusters separated by unnatural amino acids was compared with the corresponding branched peptide lacking unnatural amino acids (C6A dimer; this peptide has clusters separated by natural amino acids; Table 1). Both peptides detected 18/41 samples from panel 3 as positive. Table 5 shows six samples in which the absorbance with the peptide containing unnatural amino acids was higher than for the corresponding peptide lacking unnatural amino acids.

Table 6 shows four reactive samples from panel 3 in which peptide 3KC7C (Table 1) had increased absorbance values compared to peptide C3 (Table 1), i.e., the presence of unnatural amino acids imparted greater sensitivity to the assay for detection of NANBH and HCV.

Furthermore, a marked improvement in specificity, measured by the ELISA procedure as described in Example 1, was also obtained with branched cluster peptide 3KC7C from the NS-4 region of HCV having clusters separated by unnatural amino acids. With peptide 3KC7C, 0/48 negative samples had absorbance values greater than 0.200 A, whereas 5/48 had absorbance values greater than 0.200 A with branched peptide C3 which lacked unnatural amino acids but had natural amino acid separating the clusters. Specificity was also improved by addition of the unnatural amino acid in peptide C8C, in that only 1/48 negative random donor samples had absorbance readings greater than 0.200 A, compared with 2/48 for peptide C6A.

TABLE 4

| HCV Positive Sample[a] | $A_{492nm}$ | |
|---|---|---|
| | C10B | T1 |
| 3-7 | 2.451 | 2.005 |
| 3-8 | 1.081 | 0.873 |
| 3-9 | 2.665 | 2.272 |
| 3-12 | 0.446 | 0.352 |
| 3-24 | 2.378 | 2.088 |
| 3-25 | 2.399 | 1.555 |
| 3-39 | 1.289 | 0.767 |

[a]See Table 6

TABLE 5

| HCV Positive Sample[a] | $A_{492nm}$ | |
|---|---|---|
| | C8C | C6A |
| 3-1 | 1.622 | 1.246 |
| 3-5 | 2.130 | 1.907 |
| 3-11 | 0.895 | 0.782 |
| 3-27 | 2.710 | 2.463 |
| 3-33 | 2.108 | 1.763 |
| 3-36 | 2.236 | 2.016 |

[a]See Table 6

TABLE 6

| HCV Positive Sample[a] | $A_{492nm}$ | |
|---|---|---|
| | 3KC7C | C3 |
| 3-7 | 0.389 | 0.350 |
| 3-14 | 2.034 | 1.670 |
| 3-29 | 1.561 | 1.350 |
| 3-41 | >3.0 | 2.570 |

[a]For Tables 4–6, the remaining samples in panel 3 were negative on both peptides or showed no improvement in using the branched hybrid peptide compared to the test or control peptides.

EXAMPLE 4

Improved NS-5 immunoreactivity conferred by a shorter branched branched peptide relative to its linear parent peptide A 17 residue branched octamer cluster peptide, C2A from the NS-5 region of HCV (Table 1), was able to detect antibody in all 23/41 samples from panel 3 that were reactive with its parent linear peptide T4, SEQ ID No. 12 a 44 residue peptide having the sequence ARPDYNPPLVETWKKP-DYYYEPPVVHGCPLPPPKSPPVPPPRKKRT. Table 7 shows five samples from panel 3 that exhibited higher absorbance values with peptide octamer C2A than with linear peptide T4.

TABLE 7

| HCV Positive Sample[a] | $A_{492nm}$ | |
|---|---|---|
| | T4 | C2A |
| 3-7 | 0.742 | 1.377 |
| 3-11 | 1.188 | 1.815 |
| 3-16 | 3.139 | 3.745 |
| 3-26 | 2.263 | 2.527 |
| 3-33 | 2.118 | 2.631 |

[a]The remaining samples in panel 3 were negative on both peptides or showed no improvement in using 17-mer compared with the 44-mer.

EXAMPLE 5

Earlier detection of NANBH-associated antibodies in a seroconversion panel using a mixture of branched peptides A mixture of dimer peptides, 3KC10B, 3KH7, C9B and C6A (1, 5, 3, 0.25 ug/ml, respectively) was coated on wells of 96-well plates and assayed using the ELISA procedure described in Example 1. The sequence of each branched peptide is provided in Table 1. The sensitivity of this mixture was compared with that of Format C peptides (described in EPO 7 A2 and consisting of peptides IIH, V and VIIIE coated at 5, 3 and 2 µg/ml, respectively) using seroconversion panel 4813 described in Example 1. Table 8 shows that seroconversion samples were consistently positive on the mixture of peptides one week before antibody was detected by Format C. Earlier samples at bleed dates of Aug. 9 and Aug. 16, 1988 show fluctuation of antibody response near the cutoff of the assay and indicate detection of passive antibodies from the transfusion of this patient that occurred Jul. 19, 1988.

TABLE 8

| Panel | Donor | Bleed Date | ALT[a] (u/L) | EIA Ratio Format C | EIA Ratio Mixture[b] |
|---|---|---|---|---|---|
| 1 | 02190D | 880809 | 40.0 | 0.108 | 1.197 |
| | | 880816 | 32.0 | 0.045 | 0.899 |
| | | 880823 | 32.0 | 0.025 | 1.044 |
| | | 880830 | 180.0 | 1.037 | 1.197 |
| | | 880928 | 401.0 | 7.193 | 3.303 |
| | | 881109 | NA | 10.185 | 10.250 |
| | | 881122 | NA | 9.770 | 11.548 |

[a]Abbreviations: ALT = Alanine amino-transferase
[b]The composition of Format C and Mixture are described in Example 5

---

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

```
Gly Cys Ser Gly Gly Ala Tyr Asp Ile Ile Ile Cys Asp Glu Leu His
 1               5                  10                  15
Ser Thr Asp Ala Thr Ser Ile Leu Gly Ile Gly Thr Val Leu Asp Gln
                20                  25                  30
Ala Glu Thr Ala Gly
                35
```

( 2 ) INFORMATION FOR SEQ ID NO:2:

( i ) SEQUENCE CHARACTERISTICS:
  ( A ) LENGTH: 40 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:2:

```
Phe Thr Phe Ser Pro Arg Arg His Trp Thr Thr Gln Gly Cys Asn Cys
 1               5                  10                  15
Ser Ile Tyr Pro Gly His Ile Thr Gly His Arg Met Ala Trp Asp Met
                20                  25                  30
Met Met Asn Trp Ser Pro Thr Ala
                35              40
```

( 2 ) INFORMATION FOR SEQ ID NO:3:

( i ) SEQUENCE CHARACTERISTICS:
  ( A ) LENGTH: 60 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:3:

```
Glu Ile Leu Arg Lys Ser Arg Arg Phe Ala Gln Ala Leu Pro Val Trp
 1               5                  10                  15
Ala Arg Pro Asp Tyr Asn Pro Pro Leu Val Glu Thr Trp Lys Lys Pro
                20                  25                  30
Asp Tyr Glu Pro Pro Val Val His Gly Cys Pro Leu Pro Pro Pro Lys
                35                  40                  45
Ser Pro Pro Val Pro Pro Pro Arg Lys Lys Arg Thr
                50                  55                  60
```

( 2 ) INFORMATION FOR SEQ ID NO:4:

( i ) SEQUENCE CHARACTERISTICS:
  ( A ) LENGTH: 39 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:4:

```
Glu Ile Pro Phe Tyr Gly Lys Ala Ile Pro Leu Glu Val Ile Lys Gly
 1               5                  10                  15
Gly Arg His Leu Ile Phe Cys His Ser Lys Lys Lys Cys Asp Glu Leu
                20                  25                  30
Ala Ala Lys Leu Val Ala Leu
                35
```

( 2 ) INFORMATION FOR SEQ ID NO:5:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:5:

```
Pro Val Val Pro Gln Ser Phe Gln Val Ala His Leu His Ala Pro Thr
 1               5                  10                  15
Gly Ser Gly Lys Ser
                20
```

( 2 ) INFORMATION FOR SEQ ID NO:6:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ser Gly Lys Pro Ala Ile Ile Pro Asp Arg Glu Val Leu Tyr Arg Glu
 1               5                  10                  15

Phe Asp Glu Met Glu Glu Cys Ser Gln His Leu Pro Tyr Ile Glu Gln
            20                  25                  30

Gly Met Met Leu Ala Glu Gln Phe Lys Gln Lys Ala Leu Gly Leu
            35                  40                  45
```

( 2 ) INFORMATION FOR SEQ ID NO:7:

( i ) SEQUENCE CHARACTERISTICS:
        ( A ) LENGTH: 30 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ser Gly Lys Pro Ala Ile Ile Pro Asp Arg Glu Val Leu Tyr Arg Glu
 1               5                  10                  15

Phe Asp Glu Met Glu Glu Cys Ser Gln His Leu Pro Tyr Ile
            20                  25                  30
```

( 2 ) INFORMATION FOR SEQ ID NO:8:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

```
Lys Gln Lys Ala Leu Gly Leu Leu Gln Thr Ala Ser Arg Gln Ala Glu
 1               5                  10                  15

Val Ile Ala Pro Ala Val Gln Thr Asn Trp Gln Lys Leu Glu Thr Phe
            20                  25                  30

Trp Ala Lys His Met Trp Asn Phe
            35                  40
```

( 2 ) INFORMATION FOR SEQ ID NO:9:

( i ) SEQUENCE CHARACTERISTICS:
        ( A ) LENGTH: 61 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

```
Ser Thr Ile Pro Lys Pro Gln Arg Lys Thr Lys Arg Asn Thr Asn Arg
 1               5                  10                  15

Arg Pro Gln Asp Val Lys Phe Pro Gly Gly Gly Gln Ile Val Gly Gly
            20                  25                  30

Val Tyr Leu Leu Pro Arg Arg Gly Pro Arg Leu Gly Val Arg Ala Thr
```

-continued

```
             3 5                          4 0                          4 5
    Arg  Lys  Thr  Ser  Glu  Arg  Ser  Gln  Pro  Arg  Gly  Arg  Arg
         5 0                      5 5                      6 0
```

( 2 ) INFORMATION FOR SEQ ID NO:10:

( i ) SEQUENCE CHARACTERISTICS:
      ( A ) LENGTH: 47 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:10:

```
    Asn  Asp  Arg  Val  Val  Val  Ala  Pro  Asp  Arg  Glu  Ile  Leu  Tyr  Glu  Ala
    1              5                        1 0                           1 5

Phe  Asp  Glu  Met  Glu  Glu  Cys  Ala  Ser  Lys  Ala  Ala  Leu  Ile  Glu  Glu
                   2 0                      2 5                      3 0

Gly  Gln  Arg  Met  Ala  Glu  Met  Leu  Lys  Ser  Lys  Ile  Gln  Gly  Leu
              3 5                      4 0                      4 5
```

( 2 ) INFORMATION FOR SEQ ID NO:11:

( i ) SEQUENCE CHARACTERISTICS:
      ( A ) LENGTH: 50 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:11:

```
    Lys  Lys  Lys  Ser  Gly  Lys  Pro  Ala  Ile  Ile  Pro  Asp  Arg  Glu  Val  Leu
    1              5                        1 0                           1 5

Tyr  Arg  Glu  Phe  Asp  Glu  Met  Glu  Glu  Cys  Ser  Gln  His  Leu  Pro  Tyr
                   2 0                      2 5                      3 0

Ile  Glu  Gln  Gly  Met  Met  Leu  Ala  Glu  Gln  Phe  Lys  Gln  Lys  Ala  Leu
              3 5                      4 0                      4 5

Gly  Leu
         5 0
```

( 2 ) INFORMATION FOR SEQ ID NO:12:

( i ) SEQUENCE CHARACTERISTICS:
      ( A ) LENGTH: 46 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:12:

```
    Ala  Arg  Pro  Asp  Tyr  Asn  Pro  Pro  Leu  Val  Glu  Thr  Trp  Lys  Lys  Pro
    1              5                        1 0                           1 5

Asp  Tyr  Tyr  Tyr  Glu  Pro  Pro  Val  Val  His  Gly  Cys  Pro  Leu  Pro  Pro
                   2 0                      2 5                      3 0

Pro  Lys  Ser  Pro  Pro  Val  Pro  Pro  Pro  Arg  Lys  Lys  Arg  Thr
              3 5                      4 0                      4 5
```

We claim:

1. A peptide composition comprising a branched peptide selected from the group consisting of:

Pro—Leu—Val—Glu—Thr—Trp—Lys—Arg—Pro—Asp—Tyr—
Glu—Pro—Pro—Val—Val—His—OCT                     C2A;

Pro—Leu—Val—Glu—Thr—Trp—Lys—Lys—Pro—Asp—Tyr—
Glu—Pro—Pro—Val—Val—His—OCT                     C2B;

Pro—Leu—Val—Glu—Thr—Trp—Lys—Lys—Pro—Glu—Tyr—

Glu—Pro—Pro—Val—Val—His—DIM    C6A;

Pro—Leu—Val—Glu—Thr—Trp—Lys—Lys—Pro—Glu—Tyr—
Glu—Pro—Pro—Val—Val—His—OCT    C6B;

Asp—Tyr—Glu—Pro—Pro—Val—Val—His—DIM    C8A;

Pro—Leu—Val—Glu—Thr—Trp—Lys—Lys—Hyp—Asp—Tyr—
Glu—Pro—Pro—Val—Val—His—DIM    C8B;

and

Pro—Leu—Val—Glu—Thr—Trp—Lys—Orn—Pro—Asp—Tyr—
Glu—Pro—Pro—Val—Val—His—DIM    C8C where OCT is lysine octamer and DIM is lysine dimer.

2. A peptide composition comprising a branched peptide selected from the group consisting of:

Gly—Arg—His—Leu—Ile—Nva—Cys—His—Ser—Lys—Lys—
Lys—Cys—Asp—Glu—Nle—Ala—Ala—Lys—Leu—Val—Ala—
Leu—Gly—DIM    C9A;

and

Glu—Ile—Pro—Phe—Tyr—Gly—Lys—Ala—Nva—Pro—Leu—
Glu—Nva—Ile—Lys—Gly—Gly—Arg—His—Leu—Ile—Nva—
Cys—His—Ser—Lys—Lys—Cys—Asp—Glu—Nle—Ala—
Ala—Lys—Leu—Val—Ala—Leu—Gly—DIM    C9B;

wherein DIM is lysine dimer.

3. A peptide composition comprising a branched peptide selected from the group consisting of:

Lys—Lys—Lys—Ser—Gly—Lys—Pro—Thr—Ile—Ile—Pro—
Asp—Arg—Glu—Ile—Leu—Tyr—Arg—Glu—Phe—Asp—Glu—
Met—Glu—Asp—Cys—Ser—Gln—His—Leu—Pro—Tyr—Ile—
Asp—Gln—Gly—Met—Met—Leu—Ala—Glu—Asn—Phe—Lys—
Gln—Lys—Ala—Leu—Gly—Leu—DIM    C3;

Asp—Cys—Ser—Gln—His—Leu—Pro—Tyr—Ile—Asp—Gln—
Gly—Met—Met—Leu—Ala—DIM    C5A;

Ile—Leu—Tyr—Arg—Glu—Phe—Asp—Glu—Met—Glu—Asp—
Cys—Ser—Gln—His—Leu—Pro—Tyr—Ile—Asp—Gln—Gly—
Met—Met—Leu—Ala—DIM    C5B;

Ser—Gly—Lys—Pro—Thr—Ile—Ile—Pro—Asp—Arg—Glu—
Ile—Leu—Tyr—Arg—Glu—Phe—Asp—Glu—Met—Glu—Asp—
Cys—Ser—Gln—His—Leu—Pro—Tyr—Ile—Asp—Gln—Gly—
Met—Met—Leu—Ala—DIM    C5C;

Lys—Lys—Lys—Ser—Gly—Lys—Pro—Thr—Ile—Ile—Pro—
Asp—Arg—Glu—Ile—Leu—Tyr—Arg—Glu—Phe—Asp—Glu—
Met—Glu—Asp—Cys—Ser—Gln—His—Leu—Pro—Tyr—Ile—
Asp—Gln—Gly—Met—Met—Leu—Ala—DIM    3KC5C;

Cys—Ser—Gln—His—Nva—Pro—Tyr—Ile—Glu—Gln—Gly—
Met—Nle—Leu—Ala—Glu—Gln—Phe—Lys—Gln—Lys—Ala—
Nva—Gly—Leu—DIM    C7A;

Leu—Tyr—Arg—Glu—Phe—Asp—Glu—Nle—Glu—Glu—Cys—
Ser—Gln—His—Nva—Pro—Tyr—Ile—Glu—Gln—Gly—Met—
Nle—Leu—Ala—Glu—Gln—Phe—Lys—Gln—Lys—Ala—Nva—
Gly—Leu—DIM    C7B;

Ser—Gly—Lys—Pro—Ala—Nva—Ile—Pro—Asp—Arg—Glu—
Nva—Leu—Tyr—Arg—Glu—Phe—Asp—Glu—Nle—Glu—Glu—
Cys—Ser—Gln—His—Nva—Pro—Tyr—Ile—Glu—Gln—Gly—
Met—Nle—Leu—Ala—Glu—Gln—Phe—Lys—Gln—Lys—Ala—
Nva—Gly—Leu—DIM    C7C;

and

Lys—Lys—Lys—Ser—Gly—Lys—Pro—Ala—Nva—Ile—Pro—
Asp—Arg—Glu—Nva—Leu—Tyr—Arg—Glu—Phe—Asp—Glu—
Nle—Glu—Glu—Cys—Ser—Gln—His—Nva—Pro—Tyr—Ile—
Glu—Gln—Gly—Met—Nle—Leu—Ala—Glu—Gln—Phe—Lys—
Gln—Lys—Ala—Nva—Gly—Leu—DIM    3KC7C;

wherein DIM is lysine dimer.

4. A peptide composition comprising a branched peptide selected from the group consisting of:

Ile—Ile—Pro—Asp—Arg—Glu—Ile—Leu—Tyr—Arg—Glu—
Phe—Asp—Glu—Met—Glu—Asp—Cys—Ser—Gln—His—Leu—
Pro—Tyr—Ile—DIM    C1A;

and

Ser—Ser—Lys—Pro—Ala—Ile—Ile—Pro—Asp—Arg—Glu—
Ile—Leu—Tyr—Arg—Glu—Phe—Asp—Glu—Met—Glu—Asp—
Cys—Ser—Gln—His—Leu—Pro—Tyr—Ile—DIM    C1B;

wherein DIM is lysine dimer.

5. A peptide composition comprising a branched peptide selected from the group consisting of:

Lys—Lys—Lys—Ile—Pro—Lys—Pro—Asn—Arg—Lys—Thr—
Lys—Arg—Asn—Thr—Gln—Arg—Arg—Pro—Asn—Asp—Val—
Lys—Phe—Pro—Gly—Gly—Gly—Asn—Ile—Val—Gly—Gly—
Val—Tyr—Leu—Val—Pro—Arg—Arg—Gly—Pro—Arg—Leu—
Gly—Leu—Arg—Ala—Thr—Arg—Lys—Thr—Thr—Glu—Arg—
Ser—Gln—Pro—Arg—Gly—Arg—Arg—DIM    C4;

Arg—Pro—Asn—Asp—Nva—Lys—Phe—Pro—Gly—Gly—Gly—
Asn—Ile—Nva—Gly—Gly—Val—Tyr—Leu—Val—Pro—Arg—
Arg—Gly—Pro—Arg—Nle—Gly—Leu—Arg—Ala—Thr—Arg—
Lys—Thr—Thr—Glu—Arg—Ser—Gln—Hyp—Arg—Gly—Arg—
Arg—DIM    C10A;

Ile—Pro—Lys—Pro—Asn—Arg—Lys—Thr—Lys—Arg—Asn—
Thr—Gln—Arg—Arg—Pro—Asn—Asp—Nva—Lys—Phe—Pro—
Gly—Gly—Gly—Asn—Ile—Nva—Gly—Gly—Val—Tyr—Leu—
Val—Pro—Arg—Arg—Gly—Pro—Arg—Nle—Gly—Leu—Arg—
Ala—Thr—Arg—Lys—Thr—Thr—Glu—Arg—Ser—Gln—Hyp—
Arg—Gly—Arg—Arg—DIM    C10B;

and

Lys—Lys—Lys—Ile—Pro—Lys—Pro—Asn—Arg—Lys—Thr—
Lys—Arg—Asn—Thr—Gln—Arg—Arg—Pro—Asn—Asp—Nva—
Lys—Phe—Pro—Gly—Gly—Gly—As—Ile—Nva—Gly—Gly—
Val—Tyr—Leu—Val—Pro—Arg—Arg—Gly—Pro—Arg—Nle—
Gly—Leu—Arg—Ala—Thr—Arg—Lys—Thr—Thr—Glu—Arg—
Ser—Gln—Hyp—Arg—Gly—Arg—Arg—DIM    CKC10B;

wherein DIM is lysine dimer.

6. A peptide composition comprising a branched peptide:

Tyr—Glu—Pro—Pro—Val—Val—His—Gly—Cys—Pro—Leu—
Pro—Pro—Pro—Lys—Ser—Pro—Pro—Val—Pro—Pro—Pro—
Arg—Lys—Lys—Arg—Thr—Ile—Ile—Pro—Asp—Arg—Glu—
Val—Leu—Tyr—Arg—Glu—Phe—Asp—Glu—Met—Glu—Glu—
Cys—Ser—Gln—His—Leu—Pro—Tyr—Ile—Pro—Lys—Pro—
Gln—Arg—Lys—Thr—Lys—Arg—Asn—Thr—Asn—Arg—Arg—

-continued

Pro—Gln—Asp—Val—Lys—Phe—Pro—Gly—Gly—Gly—Gln—
Ile—Val—Gly—DIM                                          H1;

wherein DIM is lysine dimer.

7. A peptide composition comprising a branched peptide:

Gly—Cys—Ser—Gly—Gly—Thr—Tyr—Asp—Ile—Ile—Ile—
Cys—Asp—Glu—Leu—His—Ser—Thr—Asp—Ala—Thr—Ser—
Ile—Val—Gly—Ile—Gly—Thr—Ile—Leu—Asp—Gln—Ala—
Glu—Thr—Ala—Gly—Arg—His—Leu—Ile—Phe—Cys—His—
Thr—Lys—Lys—Lys—Cys—Asp—Glu—Leu—Ala—Ser—Lys—
Leu—Val—Ala—Leu—Gly—Met—OCT                             H3;

wherein OCT is lysine Octamer.

8. A peptide composition comprising a branched peptide selected from the group consisting of:

Tyr—Glu—Pro—Pro—Val—Val—His—Gly—Arg—His—Leu—
Ile—Phe—Cys—His—Thr—Lys—Lys—Lys—Cys—Asp—Glu—
Leu—Ala—Ser—Lys—Leu—Val—Ala—Gly—Met—OCT        H4A;

and

Pro—Leu—Val—Glu—Thr—Trp—Lys—Lys—Pro—Asp—Tyr—
Glu—Pro—Pro—Val—Val—His—Gly—Arg—His—Leu—Ile—
Phe—Cys—His—Thr—Lys—Lys—Lys—Cys—Asp—Glu—Leu—
Ala—Ser—Lys—Leu—Val—Ala—Leu—Gly—Met—OCT         H4B;

wherein OCT is lysine Octamer.

9. A peptide composition comprising a branched peptide selected from the group consisting of:

Ile—Glu—Gln—Gly—Met—Met—Leu—Ala—Glu—Asn—Phe—
Lys—Gln—Lys—Ala—Leu—Gly—Leu—Pro—Arg—Arg—Gly—
Pro—Arg—Leu—Gly—Leu—Arg—Ala—Thr—Arg—Lys—Thr—
Thr—Glu—Arg—Ser—Gln—Pro—Arg—Gly—Arg—Met—OCT
                                                         H6A;

Ser—Gly—Lys—Pro—Ala—Ile—Ile—Pro—Glu—Arg—Glu—
Val—Ile—Glu—Gln—Gly—Met—Met—Leu—Ala—Glu—Asn—
Phe—Lys—Gln—Lys—Ala—Leu—Gly—Leu—Pro—Arg—Arg—
Gly—Pro—Arg—Leu—Gly—Leu—Arg—Ala—Thr—Arg—Lys—
Thr—Thr—Glu—Arg—Ser—Gln—Pro—Arg—Gly—Arg—Met—
OCT                                                      H6B;

Ser—Gly—Lys—Pro—Thr—Ile—Ile—Pro—Asp—Arg—Glu—
Ile—Leu—Tyr—Arg—Glu—Phe—Asp—Glu—Met—Glu—Asp—
Cys—Ser—Gln—His—Leu—Pro—Tyr—Ile—Asp—Gln—Gly—
Met—Met—Leu—Ala—Glu—Asn—Phe—Lys—Gln—Lys—Ala—
Leu—Gly—Leu—Val—Lys—Phe—Pro—Gly—Gly—Gly—Gln—
Ile—DIM                                                  H7;

and

Lys—Lys—Lys—Ser—Gly—Lys—Pro—Thr—Ile—Ile—Pro—
Asp—Arg—Glu—Ile—Leu—Tyr—Arg—Glu—Phe—Asp—Glu—
Met—Glu—Asp—Cys—Ser—Gln—His—Leu—Pro—Tyr—Ile—
Asp—Gln—Gly—Met—Met—Leu—Ala—Glu—Asn—Phe—Lys—
Gln—Lys—Ala—Leu—Gly—Leu—Vla—Lys—Phe—Pro—Gly—
Gly—Gly—Gln—Ile—DIM                                     3KH7 where OCT is lysine octamer and DIM is lysine dimer.

10. A peptide composition comprising a branched peptide selected from the group consisting of:

Leu—Tyr—Arg—Glu—Phe—Asp—Glu—Met—Glu—Asp—Cys—
Ser—Gln—His—Leu—Pro—Tyr—Ile—Pro—Lys—Pro—Asn—
Arg—Lys—Thr—Lys—Arg—Asn—Thr—Gln—Arg—Arg—Pro—
Asn—Asp—Val—Lys—Phe—Pro—Gly—Gly—Gly—Asn—Ile—
Val—Gly—Met—OCT                                         H2A;

-continued

Pro—Asp—Arg—Glu—Ile—Leu—Tyr—Arg—Glu—Phe—Asp—
Glu—Met—Glu—Asp—Cys—Ser—Gln—His—Leu—Pro—Tyr—
Ile—Pro—Lys—Pro—Asn—Arg—Lys—Thr—Lys—Arg—Asn—
Thr—Gln—Arg—Arg—Pro—Asn—Asp—Val—Lys—Phe—Pro—
Gly—Gly—Gly—Asn—Ile—Val—Gly—Met—OCT                    H2B;

Ile—Ile—Pro—Asp—Arg—Glu—Ile—Leu—Tyr—Arg—Glu—
Phe—Asp—Glu—Met—Glu—Asp—Cys—Ser—Gln—His—Leu—
Pro—Tyr—Ile—Pro—Lys—Pro—Asn—Arg—Lys—Thr—Lys—
Arg—Asn—Thr—Gln—Arg—Arg—Pro—Asn—Asp—Val—Lys—
Phe—Pro—Gly—Gly—Asn—Ile—Val—Gly—Met—OCT               H2C;

Ile—Ile—Pro—Asp—Arg—Glu—Ile—Leu—Tyr—Arg—Glu—
Phe—Asp—Glu—Met—Glu—Asp—Cys—Ser—Gln—His—Leu—
Pro—Tyr—Ile—Pro—Lys—Pro—Asn—Arg—Lys—Thr—Lys—
Arg—Asn—Thr—Gln—Arg—Arg—Pro—Asn—Asp—Val—Lys—
Phe—Pro—Gly—Gly—Gly—Asn—Ile—Val—Gly—Lys—OCT
                                                         H2CK;

Ser—Gly—Lys—Pro—Ala—Ile—Ile—Pro—Asp—Arg—Glu—
Ile—Leu—Tyr—Arg—Glu—Phe—Asp—Glu—Met—Glu—Asp—
Cys—Ser—Gln—His—Leu—Pro—Tyr—Ile—Pro—Lys—Pro—
Asn—Arg—Lys—Thr—Lys—Arg—Asn—Thr—Gln—Arg—Arg—
Pro—Asn—Asp—Val—Lys—Phe—Pro—Gly—Gly—Gly—Asn—
Ile—Val—Gly—Met—OCT                                     H2D;

and

Ser—Ser—Lys—Pro—Ala—Ile—Ile—Pro—Asp—Arg—Glu—
Ile—Leu—Tyr—Arg—Glu—Phe—Asp—Glu—Met—Glu—Asp—
Cys—Ser—Gln—His—Leu—Pro—Tyr—Ile—Pro—Lys—Pro—
Asn—Arg—Lys—Thr—Lys—Arg—Asn—Thr—Gln—Arg—Arg—
Pro—Asn—Asp—Val—Lys—Phe—Pro—Gly—Gly—Gly—Asn—
Ile—Val—Gly—Lys—OCT                                     H2DK;

wherein OCT is lysine Octamer.

11. An immunoassay for detecting NANBH-associated antibodies using a peptide composition according to any one of claims 1–10.

12. A kit for detection or diagnosis of NANBH or HCV infection comprising a first container adapted to contain a peptide composition according to any one of claims 1–10.

13. An ELISA test kit for detection and diagnosis of NANABH or HCV infection comprising:

(a) a container having a solid phase coated with the peptide composition according to ally one of claims 1–10;

(b) a negative control sample;

(c) a positive control sample;

(d) specimen diluent; and (e) antibodies to human IgG. and antibodies labeled with a reporter molecule.

14. A peptide composition comprising peptides 3KC10B, C9B, C6A and 3KH7.

15. A peptide composition comprising peptides 3KH7, C6A and C4.

16. A peptide composition comprising peptides C3, C4 and C2B.

17. A peptide composition comprising peptides C4, C9B, C6A and 3KH7.

18. A method of detecting NANBH-associated antibodies which comprises using an effective amount of a peptide composition according to any one of claims 14–17 in an immunoassay procedure.

19. The method of claim 18 wherein said immunoassay procedure comprises contacting said peptide composition with a body fluid, tissue or tissue extract in an immunoassay procedure for a time sufficient to form a complex between said peptide composition and any antibody in said fluid, said tissue, or said tissue extract, and subjecting said complex to a detecting means.

20. A kit for detection of HCV antibodies comprising a container having a solid phase coated with the peptide composition of any one of claims 14–17.

21. An ELISA test kit for detection HCV antibodies comprising:

(a) a container having a solid phase coated with the peptide composition of any one of claims 14–17, (b) a negative control sample;

(c) a positive control sample;

(d) specimen diluent; and (e) antibodies to human IgG, said antibodies labeled with a reporter molecule.

* * * * *